(12) United States Patent
Moon et al.

(10) Patent No.: US 11,344,588 B2
(45) Date of Patent: *May 31, 2022

(54) LACTOBACILLUS PLANTARUM CJLP17 HAVING ANTIVIRAL AND IMMUNOMODULATORY EFFICACIES AND COMPOSITION COMPRISING THE SAME

(71) Applicant: CJ CHEILJEDANG CORPORATION, Seoul (KR)

(72) Inventors: Ho Jin Moon, Seoul (KR); Hee-yeon Kim, Seoul (KR); Seo Hyung Woo, Seoul (KR); Kyung Min Lee, Seoul (KR); Yoon Tack Jang, Seoul (KR); Sung Hun Kim, Seoul (KR); Jongsu Eun, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/979,725

(22) PCT Filed: May 3, 2019

(86) PCT No.: PCT/KR2019/005351
§ 371 (c)(1),
(2) Date: Sep. 10, 2020

(87) PCT Pub. No.: WO2019/212299
PCT Pub. Date: Nov. 7, 2019

(65) Prior Publication Data
US 2021/0038657 A1 Feb. 11, 2021

(30) Foreign Application Priority Data
May 3, 2018 (KR) .................. 10-2018-0051380

(51) Int. Cl.
| | | |
|---|---|---|
| *A61K 39/02* | (2006.01) | |
| *A61K 35/747* | (2015.01) | |
| *A23K 50/30* | (2016.01) | |
| *A23K 50/60* | (2016.01) | |
| *A23K 10/18* | (2016.01) | |
| *A23L 33/10* | (2016.01) | |
| *A23L 33/135* | (2016.01) | |
| *A61P 31/14* | (2006.01) | |
| *A61P 31/04* | (2006.01) | |
| *A61K 9/00* | (2006.01) | |
| *C12N 1/04* | (2006.01) | |
| *C12N 1/20* | (2006.01) | |
| *A61K 35/00* | (2006.01) | |
| *C12R 1/25* | (2006.01) | |

(52) U.S. Cl.
CPC .......... *A61K 35/747* (2013.01); *A23K 10/18* (2016.05); *A23K 50/30* (2016.05); *A23K 50/60* (2016.05); *A23L 33/127* (2016.08); *A23L 33/135* (2016.08); *A61K 9/0056* (2013.01); *A61P 31/04* (2018.01); *A61P 31/14* (2018.01); *C12N 1/04* (2013.01); *C12N 1/205* (2021.05); *A23V 2002/00* (2013.01); *A23Y 2220/67* (2013.01); *A61K 2035/115* (2013.01); *C12R 2001/25* (2021.05)

(58) Field of Classification Search
None
See application file for complete search history.

(56) References Cited

U.S. PATENT DOCUMENTS

| | | |
|---|---|---|
| 9,572,845 B2 | 2/2017 | Kim et al. |
| 9,572,846 B2 | 2/2017 | Kim et al. |
| 10,093,995 B2 | 10/2018 | Kim et al. |
| 10,130,666 B2 | 11/2018 | Kim et al. |
| 2011/0020395 A1 | 1/2011 | Benyacoub et al. |

FOREIGN PATENT DOCUMENTS

| | | |
|---|---|---|
| CN | 108102959 A | 6/2018 |
| KR | 10-2003-0063961 A | 7/2003 |
| KR | 10-2010-0063503 A | 6/2010 |
| KR | 10-2011-0000854 A | 1/2011 |
| KR | 10-2011-0046020 A | 5/2011 |
| KR | 10-2012-0064416 A | 6/2012 |
| KR | 10-2012-0111608 A | 10/2012 |
| KR | 10-2013-0056264 A | 5/2013 |
| KR | 10-2014-0022506 A | 2/2014 |
| KR | 10-2015-0044764 A | 4/2015 |
| KR | 10-2017-0009458 A | 1/2017 |
| KR | 10-2017-0072825 A | 6/2017 |
| KR | 10-2019-0063795 A | 6/2019 |

OTHER PUBLICATIONS

Lee et al., "The Effect of *Lactobacillus plantarum* CLP-1 on the Swine Viruses," *Korean Society for Biotechnology and Bioengineering Journal* 26:62-68 (2011) (w/English Abstract).

Lee et al., "Effect of *Lactobacillus plantarum* CJLP243 on the growth performance and cytokine response of weaning pigs challenged with enterotoxigenic *Escherichia coli*," *J. Anim. Sci.* 90:3709-3717 (2012).

Lee et al., "Differential Cytokine Regulatory Effect of Three *Lactobacillus* Strains Isolated from Fermented Foods," *J. Microbiol. Biotechnol.* 26(9):1517-1526 (2016).

Pensaert et al., "A New Coronavirus-Like Particle Associated With Diarrhea in Swine," *Archives of Virology* 58:243-241 (1978).

Shintawati et al., "*Lactobacillus plantarum* modulatory Effect on the Secretion of Interleukin-10,TGFB, and Fibronectin in Macrophages and Skin Dermal Fibroblasts Culture," *International Journal of Science and Research (IJSR)* ISSN (Online):2319-7064 Index Copernicus Value (2015):78.96 | Impact Factor (2015):6.391 (6 pages).

(Continued)

*Primary Examiner* — Jennifer E Graser
(74) *Attorney, Agent, or Firm* — Seed IP Law Group LLP

(57) ABSTRACT

The present disclosure relates to a novel *Lactobacillus plantarum* CJLP17 strain having acid resistance, bile resistance, and an immune-enhancing activity, and to a composition comprising the *Lactobacillus plantarum* CJLP17 strain.

20 Claims, 6 Drawing Sheets
Specification includes a Sequence Listing.

(56) References Cited

OTHER PUBLICATIONS

Sirichokchatchawan et al., "Protective Effects of Cell-Free Supernatant and Live Lactic Acid Bacteria Isolated from Thai Pigs Against a Pandemic Strain of Porcine Epidemic Diarrhea Virus," *Probiotics & Antimicro. Prot.* 10:383-390 (2018).

Song et al., "Porcine epidemic diarrhoea virus: a comprehensive review of molecular epidemiology, diagnosis, and vaccines," *Virus Genes* 44:167-175 (2012).

Boricha et al., "In vitro evaluation of probiotic properties of *Lactobacillus* species of food and human origin," *LWT—Food Science and Technology* 106:201-208 (2019).

U.S. Appl. No. 16/618,745, filed Dec. 2, 2019, Lactobacillus Plantarum CJLP475 Strain Having Antiviral and Immunomodulatory Effects and Composition Comprising the Same.

U.S. Appl. No. 16/619,050, filed Dec. 3, 2019, Composition Comprising Lactobacillus Plantarum CJLP475 Strain and Lactobacillus Plantarum CJLP17 Strain and Use Thereof.

U.S. Appl. No. 16/619,804, filed Dec. 5, 2019, Composition Comprising Lactobacillus Plantarum CJLP475 Strain and Lactobacillus Plantarum CJLP243 Strain and Use Thereof.

[FIG. 1]
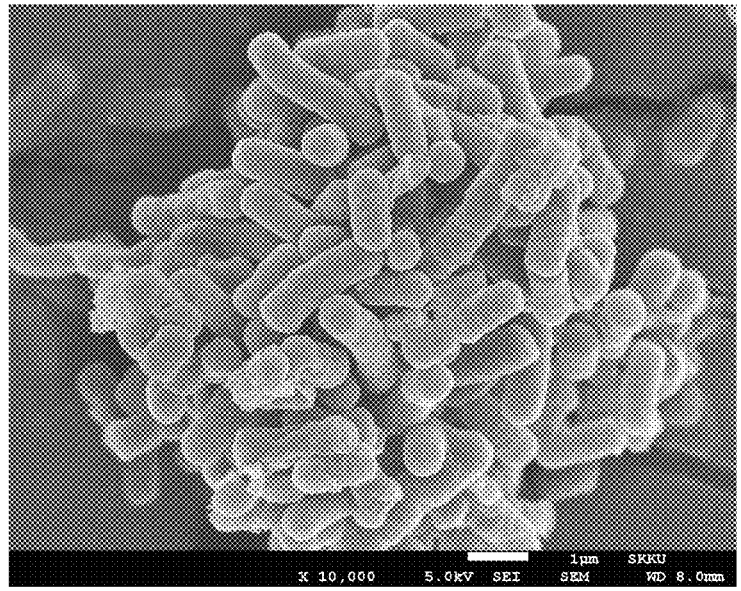
[FIG. 2]
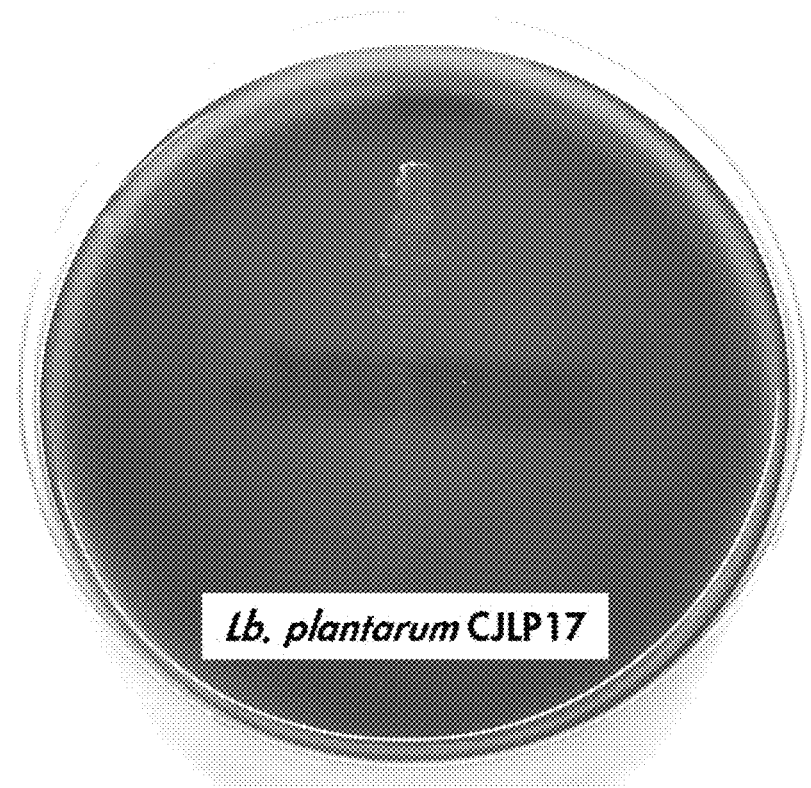

[FIG. 3]
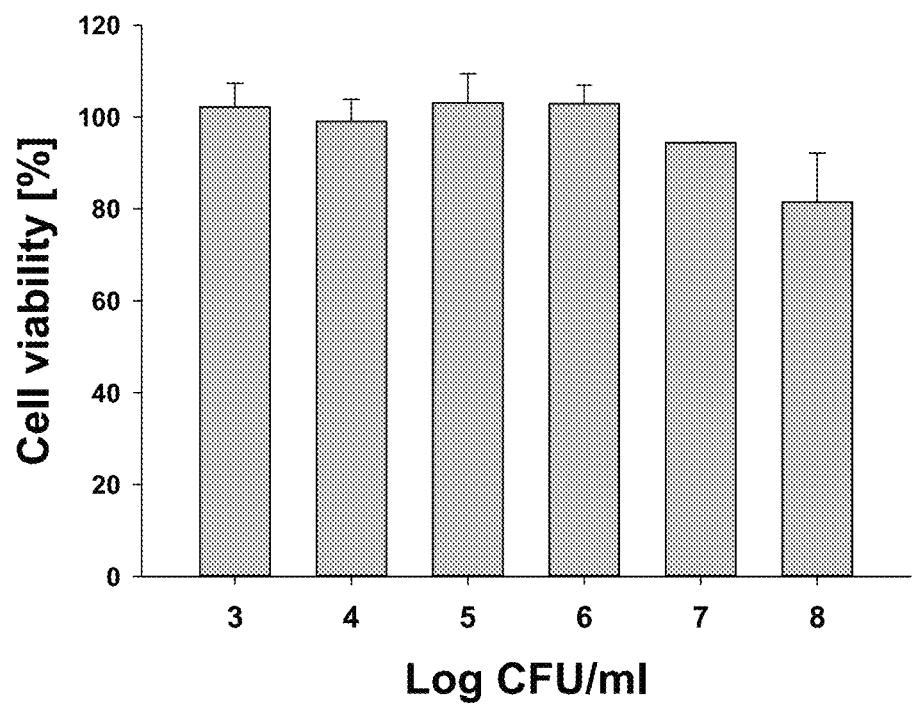

[FIG. 4]
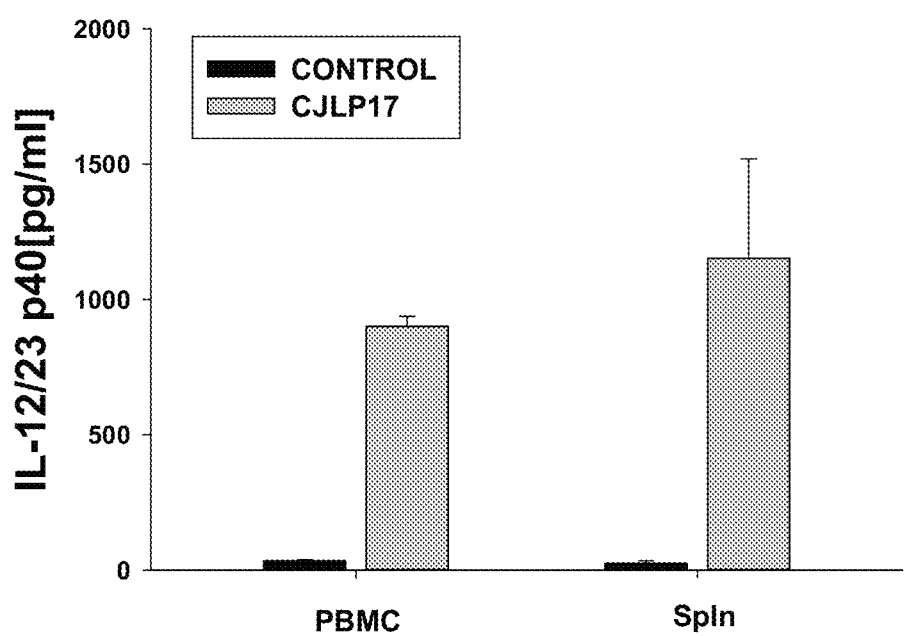

[FIG. 5]
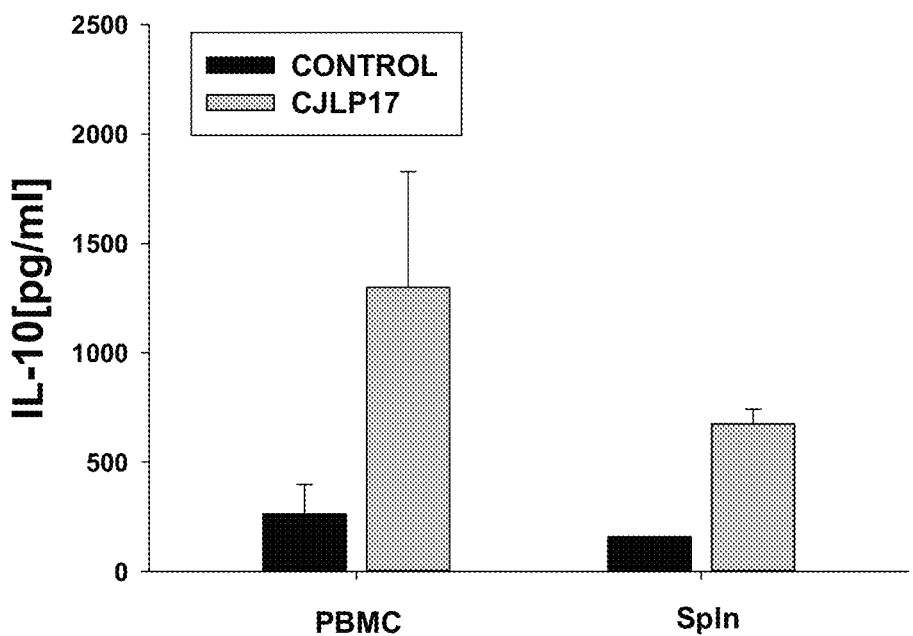
[FIG. 6]
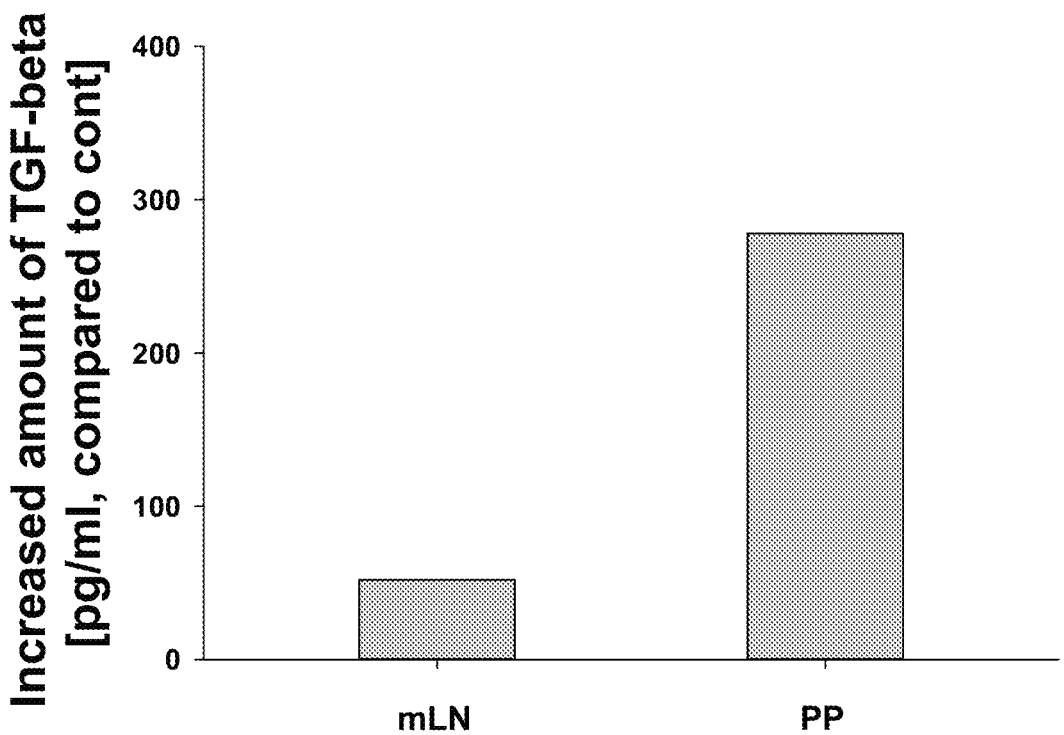

[FIG. 7]
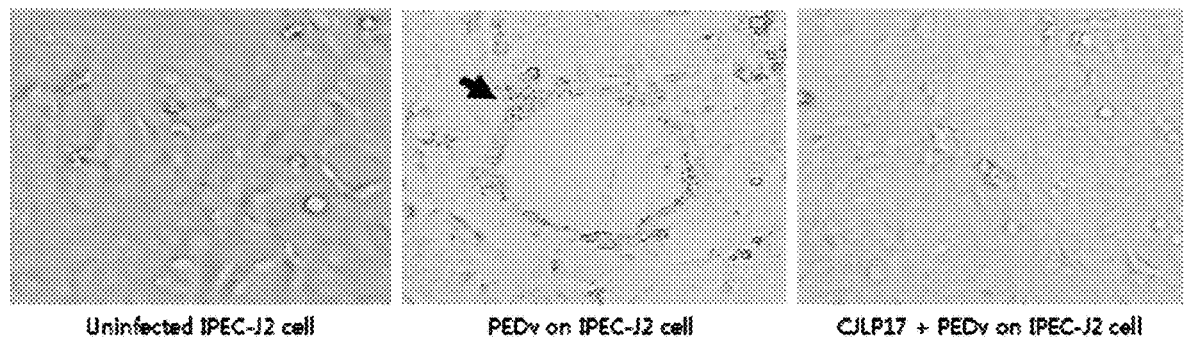
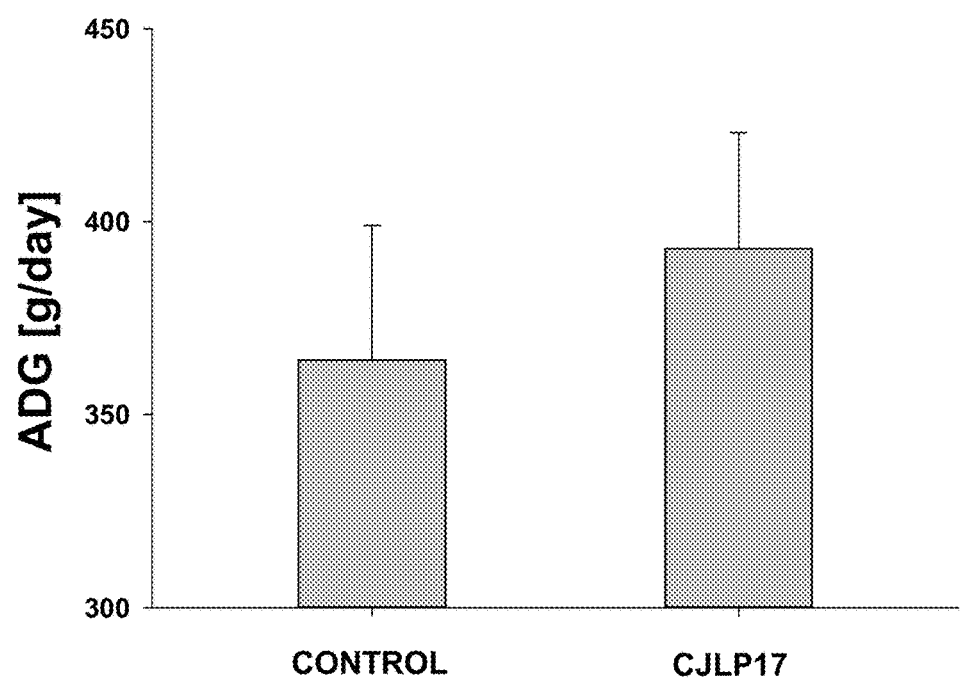
[FIG. 8]

[FIG. 9]
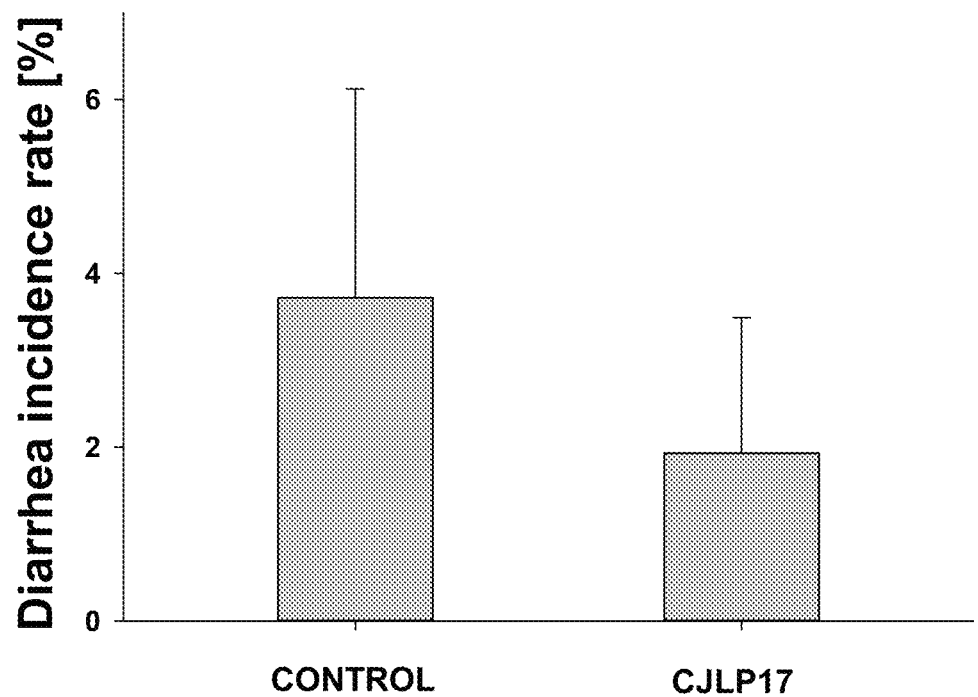

LACTOBACILLUS PLANTARUM CJLP17 HAVING ANTIVIRAL AND IMMUNOMODULATORY EFFICACIES AND COMPOSITION COMPRISING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_471USPC_SEQUENCE_LISTING.txt. The text file is 2.7 KB, was created on Sep. 3, 2020, and is being submitted electronically via EFS-Web.

TECHNICAL FIELD

The present disclosure relates to a *Lactobacillus plantarum* CJLP17 strain having acid resistance, bile resistance, and an immune-enhancing activity. Specifically, the present disclosure relates to a composition, a feed additive, and a functional food, which include the *Lactobacillus plantarum* CJLP17 strain and a culture thereof.

BACKGROUND ART

In the current livestock industry, livestock are killed due to highly contagious viral diseases, and this often leads to economic damage to farms. In particular, in the swine industry, infectious diseases caused by viruses and germs, such as the four major chronic wasting diseases (i.e., porcine respiratory disease complex, postweaning multisystemic wasting syndrome, porcine reproductive and respiratory syndrome, and porcine epidemic diarrhea), have caused huge economic losses.

Among them, porcine epidemic diarrhea is a porcine digestive disease caused by the infection of porcine epidemic diarrhea virus (PEDV), a member of the coronavirus family. The virus proliferates in the villi of the small intestine and large intestine and causes acute enteritis, vomiting, and watery diarrhea in pigs of all ages, especially in piglets. In particular, the damage is severe mainly in winter, from November to April, and it is known that the mortality rate of pre-weaning piglets within 1 week of birth is about 50%, and in severe cases, the mortality rate can reach almost 100% due to extreme dehydration.

The PED virus was first recognized in Europe in 1971 (Oldham J., Letter to the editor. *Pig Farming*, 1972, 10:72-73), and Gla-type PEDV CV777 was further detected and isolated in Belgium in 1976 (Pensaert M B et al., A new coronavirus-like particle associated with diarrhea in swine. *Arch Virol.*, 1978, 58:243-247). The virus spread throughout Europe in the 1980s, and outbreaks occurred in East Asian countries including China, Korea, Japan, Taiwan, etc. in the 1990s. Further, G2b-type PEDV, which is more virulent than the Gla-type, first emerged in China in 2010. This new type of PEDV has spread to North America (the United States and Canada) as well as to Southeast Asia and Europe, causing severe damage (Song D. et al., Porcine epidemic diarrhoea virus: a comprehensive review of molecular epidemiology, diagnosis, and vaccines, *Virus Genes*, 2012, 44:167-175). In 2013, the damage was estimated to be about 2.2 trillion won due to the loss of productivity in the US swine industry. In Korea, it is reported that PEDV outbreaks occur annually in 20% to 40% of pig farms, causing 6% of the total pigs to be killed. It is also reported that the infection rate of the vehicles entering and leaving slaughterhouses reaches about 60% (Korea Rural Economic Institute, Korea Swine Veterinary Association).

Thus far, the only way to fundamentally prevent the G2b-type PED virus has been thorough sterilization. Many farms use an artificial infection method or an inoculation of the existing Gla-type PEDV vaccine to prevent damage caused by viral diseases, but there is a limitation in preventing the G2b-type PEDV infection. In order to overcome such problems, the development of agents for prevention and treatment of PED virus (vaccines, etc.) and treatment (IgY, essential oil, organic acid, probiotics, etc.) is actively underway. In particular, a method of enhancing immunity using a functional material that stimulates the immune system in vivo while having an antiviral effect has recently been studied.

Immunity is generally divided into innate immunity and adaptive immunity. Innate immunity is a system that instantly defends pathogen infection from the first line, acting directly on invaders (antigens) or inducing adaptive immunity. Adaptive immunity is a more complex and precise system that recognizes and removes invaders, or acts as a memory for the corresponding invaders, thereby providing more permanent immune functions compared to the innate immunity. Dendritic cells (DCs), macrophages, and natural killer cells, which are antigen-presenting cells related to innate immunity, directly serve innate immune functions and possess receptors that assist in activation of various types of T cells, thereby secreting cytokines. Adaptive immunity is a secondary defense system against antigens that have entered the body, and is a specific immune response carried out by B lymphocytes and T lymphocytes. The immune responses controlled by antigen-activated T cells include a cytotoxic T cell response, a helper T cell response, etc. Naive CD4 T cells, which act as precursors to these T cells, secrete interleukin-12 (IL-12) and induce a cytotoxic T lymphocyte (CTL) response that eradicates intracellular pathogens, or secrete interleukin-4 (IL-4) and thereby induce a response that specifically eradicates extracellular pathogens (antibody secretion of B cells). In addition, the above-enumerated immune cells respond in an appropriate manner to invaders that have entered the body through an elaborate and complex process, by secreting TGF-beta (beta transforming growth factor) to suppress excessive immune responses such as an inflammatory reaction, stimulating the production of antibodies by transforming B cells into plasma cells in response to the secretion of TGF-beta and interleukin-6 (IL-6), or inducing an immune response (Th17) to eradicate false autoimmunity and extracellular pathogens.

DISCLOSURE

Technical Problem

Under these circumstances, the present inventors have completed the present disclosure by isolating and identifying a novel microorganism capable of activating the immune system while exhibiting an inhibitory activity against the above-mentioned virus, and confirming its activity.

Technical Solution

It is one object of the present disclosure to provide a *Lactobacillus plantarum* CJLP17 strain deposited under accession No. KCCM12249P, having acid resistance, bile resistance, and an immune-enhancing activity.

It is another object of the present disclosure to provide a composition including the *Lactobacillus plantarum* CJLP17 strain or a culture thereof.

It is still another object of the present disclosure to provide a feed additive including the *Lactobacillus plantarum* CJLP17 strain or a culture thereof.

It is yet another object of the present disclosure to provide a functional food including the *Lactobacillus plantarum* CJLP17 strain or a culture thereof.

Advantageous Effects

The *Lactobacillus plantarum* CJLP17 strain of the present disclosure has excellent acid resistance and bile resistance, and can thus be provided as a probiotic. The CJLP17 strain activates immune cells in vivo and thereby allows for regulation of immune functions, and particularly exhibits an excellent inhibitory activity against porcine epidemic diarrhea virus. In addition, it can be found that when livestock is orally administered with the *Lactobacillus plantarum* CJLP17 strain of the present disclosure, it not only significantly reduces the diarrhea incidence rate through the immunomodulatory effect, but also shows an effect of improving average daily gain (ADG). Accordingly, the present disclosure can provide a novel *Lactobacillus plantarum* CJLP17 strain having an antiviral activity against PEDV, an immune-enhancing activity, and an effect of improving average daily gain and reducing diarrhea incidence rate in livestock, and thus, the strain can be effectively used for a pharmaceutical composition, a food composition, or a feed composition.

BRIEF DESCRIPTION OF DRAWINGS

FIG. 1 shows an electron microscope image of CJLP17.

FIG. 2 shows an image of blood agar plate confirming hemolytic activity of the strain.

FIG. 3 is a graph confirming cytotoxicity of CJLP17.

FIG. 4. is a graph showing measurement results of IL-12 secretion after culturing splenocytes (denoted as Spin in the graph) and peripheral blood mononuclear cells (denoted as PBMC in the graph) of pigs.

FIG. 5 is a graph showing measurement results of IL-10 secretion after culturing splenocytes (denoted as Spin in the graph) and peripheral blood mononuclear cells (denoted as PBMC in the graph) of pigs.

FIG. 6 is a graph showing an increase (pg/mL) compared to a negative control by measuring secretion of TGF-beta after culturing mesenteric lymph node (denoted as mLN in the graph) and Peyer's patch cells (denoted as PP in the graph).

FIG. 7 shows microscope images illustrating the inhibitory effect against PED virus infection by the *Lactobacillus plantarum* CJLP17.

FIG. 8 is a graph showing the effect of oral administration of the CJLP17 on the mean value of ADG in weaned piglets.

FIG. 9 is a graph showing the effect of oral administration of CJLP17 on the diarrhea incidence rate in weaned piglets.

BEST MODE FOR CARRYING OUT THE INVENTION

Hereinafter, the present disclosure will be described in more detail. Meanwhile, each description and embodiment disclosed herein can be applied to other descriptions and embodiments, respectively. That is, all combinations of various elements disclosed herein fall within the scope of the present disclosure. Further, the scope of the present disclosure is not limited by the specific description below.

In one aspect of the present disclosure to overcome the objects above, there is provided a *Lactobacillus plantarum* CJLP17 strain deposited under accession No. KCCM12249P, having acid resistance, bile resistance, and an immune-enhancing activity.

As used herein, the term "*Lactobacillus*" refers to a microorganism belonging to the genus of aerobic or facultative anaerobic gram-positive *bacillus* widely distributed in nature. Microorganisms belonging to the genus *Lactobacillus* include *Lactobacillus plantarum*, etc. The present inventors provide a novel strain belonging to the *Lactobacillus plantarum*, which was deposited under accession No. KCCM12249P. This corresponds to a probiotic strain, is harmless to the human body, and can be used without side effects.

As used herein, the term "probiotics" refers to live bacteria that enter the body and provide a healthy benefit. Most of the probiotics known so far have been consumed through fermented milk products made from lactic acid bacteria such as *Lactobacillus*. In recent years, however, probiotics are available on the market in the form of fermented milk, granules, powder, etc., containing some strains such as *Bifidobacterium* and *Enterococcus*, in addition to *Lactobacillus*.

As used herein, the term "acid resistance" refers to the property of withstanding high acidity. If probiotics are acid-resistant, they can be prevented from being degraded or damaged even when exposed to strong acidic conditions in the stomach, by consumption through oral administration.

As used herein, the term "bile resistance" refers to the resistance to digestive enzymes in the bile. The bile is made in the liver and stored in the gallbladder, and is a weak alkaline greenish-brown liquid that helps the digestion of fat in the duodenum of the small intestine, and contains various enzymes that help digestion and absorption by emulsifying fat. The bile is one of the major causes of reducing the effect of probiotic administration as it acts on probiotics ingested through oral administration.

Specifically, the *Lactobacillus plantarum* CJLP17 strain of the present disclosure was obtained by isolation from the feces and colostrum of sows and piglets in domestic farms where the porcine epidemic diarrhea virus had occurred. The morphological characteristics of the strain of the present disclosure are that the strain is a gram-positive *bacillus* and is represented by the 16s rDNA nucleotide sequence of SEQ ID NO: 1. The nucleotide sequence was analyzed and found to be about 99% homologous with *Lactobacillus plantarum*. Accordingly, the present inventors deposited the novel isolated *Lactobacillus plantarum* CJLP17 strain at the Korean Culture Center of Microorganisms on Apr. 13, 2018, with accession No. KCCM12249P.

In order to stably maintain the *Lactobacillus plantarum* CJLP17 strain of the present disclosure for a long period of time, the strain may be stored by dissolving the cells in a storage solution prepared by mixing a certain amount of glycerol in water at −70° C., or may be freeze-dried by suspending the cells in sterilized 10% skim milk, but it is not limited thereto.

The *Lactobacillus plantarum* CJLP17 may have an antibacterial activity against pathogenic microorganisms.

As used herein, the term "antibacterial" refers to the activity of preventing or treating infection of bacteria by inhibiting the growth or proliferation of bacteria including pathogenic microorganisms.

As used herein, the "pathogenic microorganism" refers to a microorganism that causes disease by being parasitic to the human body. The term "pathogenicity" refers to the ability of a pathogen to infect a host and cause disease, and may collectively refer to the permeability, proliferation, and toxin productivity of bacteria or yeast. Examples of the pathogenic microorganism may include at least one pathogenic microorganism selected from the group consisting of *E. coli*, enterotoxigenic *E. coli*, *Staphylococcus aureus*, *Salmonella typhimurium*, and *Vibrio parahaemolyticus*, but are not limited thereto.

The *Lactobacillus plantarum* CJLP17 strain of the present disclosure has an antibacterial activity against pathogenic microorganisms, but not all common microorganisms belonging to the genus *Lactobacillus* have an antibacterial activity against pathogenic microorganisms.

The *Lactobacillus plantarum* CJLP17 strain of the present disclosure may not exhibit a hemolytic activity against red blood cells. Hemolysis refers to the destruction of red blood cells and the release of hemoglobin to the surrounding area, and is an action by which the red blood cells are hemolyzed by enzymes produced from harmful bacteria in vivo. Therefore, the CJLP17 is recognized as a stable microorganism that does not cause hemolysis in the blood vessels even if it is administered in vivo.

In addition, the *Lactobacillus plantarum* CJLP17 strain of the present disclosure may have a weak resistance or no resistance to antibiotics. The antibiotics may specifically be, but are not limited to, ampicillin, clindamycin, gentamicin, kanamycin, erythromycin, ampicillin/sulbactam, chloramphenicol, or streptomycin. Accordingly, even when the CJLP17 is used in pharmaceuticals, health functional foods, feed additives, etc., it has no resistance to antibiotics, and thus, the probability of causing related pharmacological effects or environmental problems is low.

The *Lactobacillus plantarum* CJLP17 strain may enhance the activation of immune cells to increase secretion of cytokines, or may be administered in vivo to promote immune function.

As used herein, the term "immune cells" refers to all cells that play a role in immune function in vivo, and can be largely divided into T cells and B cells. The immune cells may include, but are not limited to, $T_h1$ or $T_h2$ cells. The *Lactobacillus plantarum* CJLP17 strain of the present disclosure may have an activity of stimulating immune cells, thereby increasing the secretion of cytokines such as IL-12, IL-10, and/or TGF-beta.

In viral diseases, which generally show a high mortality rate, necrosis of cells or tissues themselves due to the virus can lead to a secondary infection and septicemia induced by other strains, an inflammatory disease caused by an overly activated immune response, or appetite reduction and dehydration. Therefore, when the antiviral efficacy (related to $T_h1$ and $T_h2$), which suppresses the viral infection, and the immune response ($T_h2$, anti-inflammation), which regulates the secondary infection and the excessive inflammation response, are simultaneously enhanced, an effective prevention and treatment effect for viral diseases can be achieved. As such, a strain that simultaneously enhances $T_h1$ and $T_h2$ with respect to providing an immune-enhancing effect through probiotics is not known in the art, and such a strain has been newly identified by the present inventors.

As used herein, the term "cytokine" refers to a glycoprotein used as a signal substance for controlling and stimulating a body defense system, and may be, for example, IL-12, IL-10, or TGF-beta, but is not limited thereto.

The strain may promote the growth of livestock or reduce a diarrhea incidence rate when administered to livestock via an oral route.

The strain may have an antiviral activity against porcine epidemic diarrhea virus (PEDV).

The porcine epidemic diarrhea virus is a coronavirus that infects enterocytes of pigs, causing porcine epidemic diarrhea which induces severe diarrhea and dehydration. When the *Lactobacillus plantarum* CJLP17 strain of the present disclosure or a culture thereof is treated, the activity and infection of PEDV can be remarkably suppressed. Thus, the composition including the *Lactobacillus plantarum* CJLP17 strain or a culture thereof may be used as an antiviral composition against PEDV, or a pharmaceutical composition for preventing or treating porcine epidemic diarrhea, a health functional food composition, a quasi-drug, or a feed composition for preventing or improving porcine epidemic diarrhea.

In another aspect of the present disclosure, there is provided a composition including the *Lactobacillus plantarum* CJLP17 strain, a culture thereof, a concentrate thereof, or a dried form thereof. Further details regarding the strain can be found by referring to the above description.

The newly isolated strain of the present disclosure may be cultured by a conventional method for culturing *Lactobacillus* strains. As the medium, a natural medium or a synthetic medium may be used. As the carbon source of the medium, for example, glucose, sucrose, dextrin, glycerol, starch, etc. may be used. As the nitrogen source, peptone, meat extracts, yeast extracts, dried yeasts, soybean, ammonium salts, nitrate, and other organic or inorganic nitrogen-containing compounds may be used, but the nitrogen source is not limited thereto. As the inorganic salts included in the medium, magnesium, manganese, calcium, iron, potassium, etc. may be used, but the inorganic salts are not limited thereto. Amino acids, vitamins, nucleic acids, and related compounds may be added to the medium in addition to the carbon source, the nitrogen source, and the components of the inorganic salts. The newly isolated strain of the present disclosure may be cultured for 12 hours to 4 days in a temperature range of 20° C. to 40° C.

Specifically, the culture broth of the newly isolated strain may be a crude culture broth containing cells, or may also be cells from which a culture supernatant is removed, or concentrated cells. The composition of the culture broth may additionally contain not only components required for conventional culture of *Lactobacillus*, but also components that act synergistically to the growth of *Lactobacillus*, and the compositions thereof may be readily selected by those skilled in the art.

In addition, the strain may be in a liquid state or a dry state, and the drying method may include, but is not limited to, air drying, natural drying, spray drying, and freeze drying.

In the composition, the concentration of the *Lactobacillus plantarum* CJLP17 strain may be $10^3$ CFU/mL to $10^8$ CFU/mL, $10^4$ CFU/mL to $10^8$ CFU/mL, $10^5$ CFU/mL to $10^8$ CFU/mL, $10^6$ CFU/mL to $10^8$ CFU/mL, $10^3$ CFU/mL to $10^7$ CFU/mL, $10^4$ CFU/mL to $10^7$ CFU/mL, $10^5$ CFU/mL to $10^7$ CFU/mL, $10^6$ CFU/mL to $10^7$ CFU/mL, but is not limited thereto.

The composition may further include a cryoprotectant or an excipient. More specifically, the composition may further include at least one cryoprotectant selected from the group consisting of glycerol, trehalose, maltodextrin, skim milk powder, and starch; and/or at least one excipient selected from the group consisting of glucose, dextrin, and skim milk. The cryoprotectant of the present disclosure may be contained in an amount of 0.01% to 20% by weight or 0.01% to 10% by weight based on the total weight of the composition. Specifically, based on the total weight of the composition, the glycerol may be contained in an amount of 5% to 20% by weight, the trehalose may be contained in an amount of 2% to 10% by weight, the maltodextrin may be contained in an amount of 2% to 10% by weight, the skim milk powder may be contained in an amount of 0.5% to 2% by weight, and the starch may be contained in an amount of 0.1% to 1% by weight in the composition. In addition, the excipient may be contained in an amount of 75% to 95% by weight or 85% to 95% by weight based on the total weight of the composition.

In addition, the method for preparing a composition including the *Lactobacillus plantarum* CJLP17 strain, a culture thereof, a concentrate thereof, or a dried form thereof may include a step of mixing an additive with the *Lactobacillus plantarum* CJLP17 strain, a culture thereof, a concentrate thereof, or a dried form thereof. The additive may be the above-described cryoprotectant or excipient.

In still another aspect, there is provided a probiotic preparation including the newly-isolated strain of the present disclosure or a culture thereof as an active ingredient.

Probiotics are fixed on the walls of the digestive tract in the intestines to prevent the establishment of harmful bacteria, and inhibit the proliferation of viruses. In addition, the beneficial digestive enzymes produced by probiotics promote growth by facilitating the absorption and utilization of nutrients.

The composition may be selected from the group consisting of foods, functional foods, feeds, feed additives, cosmetic compositions, pharmaceutical compositions, and quasi-drugs.

The composition including the *Lactobacillus plantarum* CJLP17 strain or a culture thereof may have an antibacterial activity against pathogenic microorganisms. The strain, pathogenic microorganism, and antibacterial activity are as described above.

Specifically, the pathogenic microorganism may be at least one selected from the group consisting of *E. coli*, enterotoxigenic *E. coli*, *Staphylococcus aureus*, *Salmonella typhimurium*, and *Vibrio parahaemolyticus*.

The composition including the *Lactobacillus plantarum* CJLP17 strain or a culture thereof may be a composition for enhancing immunity.

In yet another aspect of the present disclosure, there is provided a feed additive or feed composition, which includes the *Lactobacillus plantarum* CJLP17 strain or a culture thereof.

The above *Lactobacillus plantarum* CJLP17 strain is as described above. Specifically, the *Lactobacillus plantarum* CJLP17 strain of the present disclosure may be added to a feed additive or a feed composition including the feed additive for the purpose of providing an antibacterial activity, promoting growth, reducing a diarrhea incidence rate, and inhibiting a viral activity.

As used herein, the term "feed additive" refers to substances added to a feed for the purpose of providing various effects, such as supplementing nutrients and preventing weight loss, promoting digestibility of cellulose in the feed, improving milk quality, preventing reproductive disorders and improving pregnancy rates, preventing high-temperature stress during the summer season, etc. The feed additive of the present disclosure belongs to a supplementary feed according to the Control of Livestock and Fish Feed Act, and may further include mineral preparations such as sodium hydrogen carbonate, bentonite, magnesium oxide, complex minerals, and trace minerals including zinc, copper, cobalt, selenium, etc.; vitamin preparations such as carotene, vitamin E, vitamin A, vitamin D, vitamin E, nicotinic acid, vitamin B complex, etc.; amino acid protective preparations such as methionine, lysine, etc.; fatty acid protective preparations such as fatty acid calcium, etc.; and live bacteria and yeast preparations such as probiotics (lactic acid bacteria), yeast culture, fungus fermented product, etc.

As used herein, the term "feed" refers to any natural or artificial diet, a single meal, etc., or a component of the single meal, which an animal eats, ingests, and digests or which is suitable for eating, ingestion, and digestion. The feed including the composition for preventing or treating metabolic diseases according to the present disclosure as an active ingredient may be prepared into various forms of feed known in the art, and may preferably include a concentrated feed, a crude feed, and/or a specialty feed.

The subjects to be raised may include any organism that can ingest the feed of the present disclosure, and may include pigs for the purpose of the present disclosure.

The content of the *Lactobacillus plantarum* CJLP17 strain in the feed composition according to the present disclosure may be properly controlled depending on the kind and age of livestock to be applied, application forms, desired effects, etc., and may be, for example, used in an amount of 0.01% to 20% by weight, but is not limited thereto.

For administration, the feed composition of the present disclosure may further include a mixture of one or more of an organic acid such as citric acid, fumaric acid, adipic acid, lactic acid, etc.; a phosphate such as potassium phosphate, sodium phosphate, polyphosphate, etc.; and a natural antioxidant such as polyphenol, catechin, tocopherol, vitamin C, green tea extract, chitosan, tannic acid, etc. If necessary, other conventional additives such as an anti-influenza agent, a buffer, a bacteriostatic agent, etc. may be added. Further, a diluent, a dispersing agent, a surfactant, a binder, or a lubricant may be additionally added to formulate the composition into an injectable preparation such as an aqueous solution, a suspension, an emulsion, etc., a capsule, a granule, or a tablet.

Additionally, the feed composition of the present disclosure may be used together with a nutrient supplement, a growth accelerator, a digestion-absorption accelerator, and a prophylactic agent, in addition to various auxiliaries such as amino acids, inorganic salts, vitamins, antioxidants, antifungal agents, antibacterial agents, etc., as auxiliary components, and the main ingredients including vegetable protein feeds such as pulverized or crushed wheat, barley, corn, etc., animal protein feeds such as blood meal, meat meal, fish meal, etc., animal fat, and vegetable fat.

When the feed composition of the present disclosure is used as a feed additive, the feed composition may be added as it is or used together with other components, or may be appropriately used according to a conventional method. The feed composition may be prepared in the administration form of an immediate-release or sustained-release formulation, in combination with a non-toxic, pharmaceutically acceptable carrier. The edible carrier may be corn starch, lactose, sucrose, or propylene glycol. A solid carrier may be in the administration form of tablets, powders, troches, etc., and a liquid carrier may be in the administration form of syrups, liquid suspensions, emulsions, solutions, etc. Further, the administration agent may include a preservative, a lubricant, a solution accelerator, or a stabilizer, and may also include other agents for improving other inflammatory diseases and substances useful for the prevention of viruses.

The feed composition according to the present disclosure may be mixed in an amount of about 10 g to 500 g, specifically 10 g to 100 g per 1 kg, based on the dry weight of the livestock feed. After being completely mixed, the feed composition may be provided as mash, or may be further subjected to a pelletizing, extensification, or extrusion process, but is not limited thereto.

In further another aspect of the present disclosure, there is provided a food composition or functional food, which includes the *Lactobacillus plantarum* CJLP17 strain or a culture thereof.

Specifically, the composition of the present disclosure may be added to a food composition for the purpose of providing an antibacterial activity, promoting growth, promoting immunity, reducing a diarrhea incidence rate, and inhibiting a viral activity. The *Lactobacillus plantarum* CJLP17 strain is as described above. The food composition may include a sitologically acceptable carrier.

The food composition of the present disclosure includes all forms of functional foods, nutritional supplements, health foods, and food additives, and these types of food composition may be prepared into various forms according to conventional methods.

When the *Lactobacillus plantarum* CJLP17 strain is used as a food additive, the *Lactobacillus plantarum* CJLP17 strain may be added as it is or used in combination with other foods or food ingredients, or may be appropriately used according to a conventional method. The amount of mixed active ingredients may appropriately be determined depending on the purpose of use (prevention, health, or therapeutic treatment). In general, at the time of preparing a food or drink, the *Lactobacillus plantarum* CJLP17 strain is added in an amount of 0.0001% to 1% by weight, specifically 0.001% to 0.1% by weight based on a raw material composition including the *Lactobacillus plantarum* CJLP17 strain. However, in the case of long-term administration for health and hygiene purposes or for the purpose of controlling health, the amount may be less than the above-described range.

There is no particular limitation on the type of the food. Examples of foods to which the above material can be added include meats, sausages, breads, chocolates, candies, snacks, confectionaries, pizzas, instant noodles, other noodles, gums, dairy products including ice creams, various kinds of soup, beverages, teas, drinks, alcoholic drinks, vitamin complexes, etc., and all health functional foods in the ordinary sense are included.

The health drink composition of the present disclosure may further contain, as additional components, various flavoring agents or natural carbohydrates, as in conventional drinks. The aforementioned natural carbohydrates may include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. Natural sweetening agents such as thaumatin, a *stevia* extract, etc.; and synthetic sweetening agents such as saccharin, aspartame, etc. may be used as the sweetening agent. A ratio of the additional components may be in a range of 0.01 to 0.04 parts by weight, specifically 0.02 to 0.03 parts by weight based on 100 parts by weight of the composition of the present disclosure.

In addition to the aforementioned components, the composition of the present disclosure may contain various nutritional supplements, vitamins, electrolytes, flavoring agents, coloring agents, pectic acid and salts thereof, alginic acid and salts thereof, organic acids, protective colloidal thickening agents, pH controlling agents, stabilizing agents, preservatives, glycerin, alcohols, carbonating agents used in carbonated drinks, etc. The ratio of such additives is not important, but is generally chosen in a range of 0.01 to 0.1 parts by weight based on 100 parts by weight of the composition of the present disclosure. Moreover, the composition of the present disclosure may contain pulp for preparing a natural fruit juice, a fruit juice drink, or a vegetable drink. The ratio of such pulp is not important, but is generally chosen in a range of 0.01 to 10 parts by weight based on 100 parts by weight of the composition of the present disclosure. Such components may be used alone or in combination.

The composition of the present disclosure, which includes the *Lactobacillus plantarum* CJLP17 strain, a culture thereof, a concentrate thereof, or a dried form thereof, may be administered to a subject. By the administration above, the composition may exhibit effects of the composition for the subject of the present disclosure (i.e., an antibacterial activity against pathogenic microorganisms, an immune-enhancing activity, etc.).

The subject may include animals which exclude or include humans. The animals may include not only humans but also all animals that need to exert the above-mentioned effects of the composition. Specifically, the animals may be mammals such as cows, horses, sheep, pigs, goats, camels, antelopes, dogs, cats, etc. As another example, the animals may be pets.

The dosage for the administration is not limited, but the composition may be administered in an amount of $10^6$ CFU/day or more, $10^7$ CFU/day or more, $10^8$ CFU/day or more, $10^9$ CFU/day or more, or $10^{10}$ CFU/day or more based on the *Lactobacillus plantarum* CJLP17 strain.

MODE FOR CARRYING OUT THE INVENTION

Hereinafter, the present disclosure will be described in more detail by way of Examples. However, these Examples are given for illustrative purposes only, and the scope of the present disclosure is not intended to be limited by these Examples.

Example 1: Isolation and Selection of Strains 1-1. Sample Collection and Isolation of Strains Samples of feces and colostrum of sows and piglets were collected from the domestic farms where chronic outbreaks of PEDV had occurred. The thus-collected samples were subjected to serial dilution, smeared on a solid MRS and BHI medium, and incubated at 37° C. for 48 hours. The strains isolated from each sample were purely isolated by transferring them to a fresh medium, and the purely isolated and incubated strains were stored in a nutrient medium supplemented with 20% glycerol at −70° C. or below. As a result, a total of 1,552 strains were collected, and strains having an excellent antiviral activity were selected through the following Examples.

1-2. Assessment of Acid Resistance and Bile Resistance of Strains

In order to select the strains that can be used as probiotics, acid resistance and bile resistance of the collected strains were assessed.

An artificial gastric juice medium was prepared for the assessment of acid resistance. More specifically, the artificial gastric juice medium was prepared by adding pepsin to a liquid MRS medium so as to adjust the pH to 2.5, followed by sterilization.

The strains of Example 1-1 were subjected to a static culture in a liquid MRS medium at 37° C. for 18 hours after the second subculture. 1% of the pre-incubated strains were inoculated to the artificial gastric juice medium and subjected to a static culture at 37° C., and the culture broth was sampled at 0 hours and 3 hours. The sampled culture broth was serially diluted and smeared on a solid MRS medium, and was incubated at 37° C. for 48 hours to measure viable cell count.

An artificial bile medium was prepared for the assessment of bile resistance. More specifically, the artificial bile medium was prepared by adding 0.5% oxgall (i.e., ox's bile) to a liquid MRS medium, followed by sterilization.

The strains of Example 1-1 were subjected to a static culture in a liquid MRS medium at 37° C. for 18 hours after the second subculture. 1% of the pre-incubated strains were inoculated to the artificial bile medium and subjected to a static culture at 37° C., and the culture broth was sampled at 0 hours and 24 hours. The sampled culture broth was serially diluted and smeared on a solid MRS medium, and incubated at 37° C. for 48 hours to measure viable cell count.

Through the above assessments, CJLP17, which was the strain having the highest acid resistance and bile resistance, was selected. The thus-selected strain was identified as the *Lactobacillus plantarum* as confirmed through the following Examples. In order to compare the acid resistance and bile resistance of the CJLP17 strain with those of the conventionally known strains, the acid resistance and bile resistance of the *Lactobacillus plantarum* standard strain (KCCM12116) obtained from the Korean Culture Center of Microorganisms were assessed in the same manner as in the above method.

TABLE 1

Acid Resistance Assessment (unit: CFU/mL)

|  | 0 hours | 3 hours |
|---|---|---|
| *Lactobacillus plantarum* CJLP17 | $1.1 \times 10^6$ | $4.0 \times 10^6$ |
| *Lactobacillus plantarum* (KCCM12116) | $2.3 \times 10^7$ | $1.3 \times 10^7$ |

TABLE 2

Bile Resistance Assessment (Unit: CFU/mL)

|  | 0 hours | 24 hours |
|---|---|---|
| *Lactobacillus plantarum* CJLP17 | $1.3 \times 10^6$ | $1.1 \times 10^7$ |
| *Lactobacillus plantarum* (KCCM12116) | $2.1 \times 10^7$ | $1.6 \times 10^6$ |

According to Tables 1 and 2 above, the number of cells of the *Lactobacillus plantarum* standard strain (KCCM12116) in the artificial gastric juice medium and the artificial bile medium decreased. As a result, it can be seen that not all commonly known *Lactobacillus plantarum* have acid resistance and bile resistance.

Meanwhile, the number of cells of the *Lactobacillus plantarum* CJLP17 strain actually increased in both media, indicating that the strain has excellent acid resistance and bile resistance.

1-3: Investigation of Morphological and Biochemical Characteristics of Strain

For the identification of the CJLP17 strain, morphological and biochemical characteristics of the strain were primarily investigated. As the morphological characteristics, the strain was gram-positive as a result of Gram staining, and was found to be *bacillus* as confirmed by electron microscopy (FIG. 1). In order to analyze the biochemical characteristics, the sugar fermentation patterns of the strain were analyzed with the API 50CHL system (biomerieux Vitek, Inc., France) (Table 3).

TABLE 3

Analysis of Sugar Fermentation Patterns of Isolated Strain

| Name of Strain | CJLP17 | Name of Strain | CJLP17 |
|---|---|---|---|
| Control | − | Esculin | − |
| Glycerol | − | Salicin | + |
| Erythritol | − | Cellobiose | + |
| D-Arabinose | − | Maltose | + |
| L-Arabinose | + | Lactose | + |
| Ribose | + | Melibiose | + |
| D-Xylose | − | Saccharose | + |
| L-Xylose | − | Trehalose | + |
| Adonitol | − | Inulin | − |
| β-Methyl-xyloside | − | Melezitose | + |
| Galactose | + | D-Raffinose | − |
| D-Glucose | + | Amidon | − |
| D-Fructose | + | Glycogen | − |
| D-Mannose | + | Xylitol | − |
| L-Sorbose | − | β-Gentiobiose | + |
| Rhamnose | − | D-Turanose | + |
| Dulcitol | −− | D-Lyxose | − |
| Inositol | − | D-Tagatose | − |
| Mannitol | + | D-Fucose | − |
| Sorbitol | + | L-Fucose | − |
| α-Methyl-D-mannoside | + | D-Arabitol | − |
| α-Methyl-D-glucoside | − | L-Arabitol | − |
| N-Acetyl glucosamine | + | Gluconate | + |
| Amygdaline | + | 2-Ceto-gluconate | − |
| Arbutin | + | 5-Ceto-gluconate | − |

+: Positive,
−: Negative 1-4. Identification of Strain

In order to more accurately identify the strain, a molecular phylogenetic method based on the DNA sequence was performed. Sequence analysis was performed as follows: the gene of 16s rDNA was amplified using PCR premix (Bioneer, Korea) and universal primers 27F (5' AGAGTTTGATCMTGGCTCAG 3') (SEQ ID NO: 2) and 1492R (5' GGTTACCTTGTTACGACTT 3') (SEQ ID NO: 3). At the time of the amplification of the gene, the total volume of the reaction solution was adjusted to 20 μL, and the reaction was performed at 94° C. for 1 minute, at 56° C. for 1 minute, and at 72° C. for 1 minute, and this cycle was repeated 30 times in total to analyze the amplified DNA sequence. The analyzed 16s rDNA nucleotide sequence of the isolated strain is represented by SEQ ID NO: 1.

As a result of the analysis, CJLP17 was identified as a microorganism having 99% homology with *Lactobacillus plantarum*. Thus, the isolated strain was named "*Lactobacillus plantarum* CJLP17", and the newly identified microorganism was deposited as *Lactobacillus plantarum* CJLP17 at the Korean Culture Center of Microorganisms on Apr. 13, 2018, with Accession No. KCCM12249P.

Example 2: Analysis of Antibacterial Activity Characteristics of CJLP17

*E. coli*, enterotoxigenic *E. coli*, *Staphylococcus aureus*, *Salmonella typhimurium*, and *Vibrio parahaemolyticus* were prepared as pathogenic microorganisms, and the antibacterial activity of CJLP17 against these pathogenic microorganisms was assessed.

The CJLP17 strain was inoculated into a liquid MRS medium and subjected to a static culture at 37° C. for 24 hours. Among the pathogenic microorganisms, *E. coli*, enterotoxigenic *E. coli, Salmonella typhimurium*, and *Staphylococcus aureus* were inoculated into a liquid BHI medium and incubated at 37° C. for 18 hours at 200 rpm, and *Vibrio parahaemolyticus* was inoculated into a liquid LB medium supplemented with 3% NaCl and incubated at 30° C. for 18 hours at 200 rpm.

10 μL of the culture broth of CJLP17 was aliquoted to a solid MRS medium and dried, which was then pre-incubated at 37° C. for 18 hours. 1% of the culture broth of the pathogenic microorganisms was independently inoculated into 10 mL of a solid BHI medium, and then the resultant was poured onto the solid MRS medium, in which CJLP17 was pre-cultured, and allowed to stand for complete solidification. Then, the size of the ring formed by incubating at 37° C. for 24 hours was measured. As the size of the ring increased, the antibacterial activity was found to be high. For comparison of the antibacterial activity, the antibacterial activity of the *Lactobacillus plantarum* standard strain (KCCM12116) was assessed in the same manner as in the method above.

TABLE 4

| Name of Strains | *E. coli* | Enterotoxigenic *E. coli* | *Staphylococcus aureus* | *Salmonella typhimurium* | *Vibrio parahaemolyticus* |
|---|---|---|---|---|---|
| CJLP17 | 5 | 8 | 8 | 7.5 | 6 |
| *L. plantarum* (KCCM12116) | 3 | 5 | 4.5 | 3 | 4 |

(Unit: mm)

As a result of measuring the size of the ring by the method above, as shown in Table 4, it was confirmed that CJLP17 exhibited a superior antibacterial activity against all pathogenic microorganisms, as compared to the *Lactobacillus plantarum* standard strain.

Example 3: Assessment of Stability of Strain

3-1. Confirmation of Hemolytic Activity of Strains

β-Hemolysis is a phenomenon in which phospholipids supplied by red blood cells are hydrolyzed by phospholipid enzymes produced by harmful bacteria, resulting in hemolysis of red blood cells. In order to determine the hemolytic activity of the CJLP17 strain, blood agar plates (sheep blood 5% agar, Hanilkomed, Korea) were used. The strain was streaked into the prepared blood agar plates and incubated at 37° C. for 24 hours to confirm the hemolysis.

As a result, as shown in FIG. 2, it was confirmed that the *Lactobacillus plantarum* CJLP17 strain did not show a hemolytic activity.

3-2. Assessment of Antibiotic Susceptibility

The CJLP17 strain was inoculated into a liquid MRS medium and subjected to a static culture at 37° C. for 24 hours. The thus-cultured bacteria were soaked in sterilized cotton swabs and smeared on a solid Mueller Hinton II medium (Difco), and then antibiotic discs were placed on the medium and incubated at 37° C. for 24 hours. Ampicillin, clindamycin, gentamicin, kanamycin, erythromycin, ampicillin/sulbactam, chloramphenicol, and streptomycin discs (Oxoid, UK) were used as antibiotic discs for the antibiotic test.

As a result of the antibiotic susceptibility test of the CJLP17 strain, it was identified that the CJLP17 strain was not resistant to the antibiotics above (Table 5). Therefore, it could be found that even if the CJLP17 strain is used in pharmaceuticals, health functional foods, feed additives, etc., problems that may arise with respect to the resistance and environmental problems are less likely to occur, considering that they have no resistance to antibiotics.

TABLE 5

Inhibition of Bacterial Growth According to Antibiotics

| Antibiotics | Radius of Growth Inhibition Area Centered Around Antibiotics (mm) CJLP17 |
|---|---|
| Amp10 (Ampicillin) | 7.5 |
| C30 (Clindamycin) | 7 |
| CN120 (Gentamicin) | 5 |
| K30 (Kanamycin) | 1.5 |
| E15 (Erythromycin) | 12 |
| SAM20 (Ampicillin/Sulbactam) | 7 |
| S10 (Chloramphenicol) | 3.5 |
| DA2 (Streptomycin) | 4.5 |

Example 4: Assessment of Cytotoxicity

In order to investigate the effect of the strain on the survival of cells, the MTS assay was carried out using (3-(4,5-dimethyl-2-yl)-5-(3-carboxymethoxyphenyl)-2-(4-sulfophenyl)-2H-tetrazolium, (promega, USA) to assess the level of cytotoxicity on IPEC-J2 cells (intestinal pig epithelium cells). Each cell was incubated on a 96-well cell culture plate and treated with CJLP17 at different concentrations from $10^3$ CFU/well to $10^8$ CFU/well. After 24 hours, the MTS solution was added to the cell culture broth, the cells were incubated for 2 hours, and the cell survival rate (%) was calculated by measuring the absorbance at 490 nm with a microplate reader.

As a result, as shown in FIG. 3, when the cells were treated at six different concentrations, it was confirmed that cell death was hardly observed at concentrations of $10^7$ CFU/mL or below, and the cells showed a survival rate of about 80% at a concentration of $10^8$ CFU/mL. Therefore, it could be confirmed that CJLP17 substantially showed no cytotoxicity at concentrations of $10^7$ CFU/mL or below.

Example 5: Assessment of Immune-Enhancing Activity

In order to confirm the immune-enhancing effect of the CJLP17 strain, IPEC-J2 cells were incubated in DMEM/F-12 medium (Dulbecco's Modified Eagle Medium: Nutrient Mixture F-12). In addition, the lymphocytes in mesenteric lymph nodes (mLN), peripheral blood mononuclear cells (PBMC), cells in Peyer's patches, and splenocytes (Spin) were collected from 21-day-old weaned piglets, and immune cells were obtained from each tissue and serum by the following method.

In order to obtain immune cells from the splenocytes and the lymphocytes in mesenteric lymph nodes, the chopped tissue was pulverized using a plunger of a syringe and a 70-micrometer cell strainer (BD Falcon), and then the cells were washed using an RPMI-1640 medium (Roswell Park Memorial Institute-1640, Gibco BRL, Grand Island, N.Y., USA). The remaining RBCs (red blood cells) were removed using an RBC lysis buffer (eBioscience, USA) prior to the last washing step. The immune cells collected after the last washing step were stained with Trypan blue and counted with a hemocytometer to be used.

In order to obtain cells in Peyer's patches, the corresponding tissues were isolated from the small intestine, and then chopped and pulverized using a surgical scissor. Subsequently, the cells were reacted in RPMI-1640 medium (pH 7.2) containing Dnase I (Roche, Germany), Dispase II (Sigma aldrich, USA), antibiotics, FBS, and 15 mM 4-(2-hydroxyethyl)-1-piperazineethanesulfonic acid (HEPES) for 1 hour to obtain single cells. Thereafter, the immune cells were obtained in the same manner as described above.

The collected blood was mixed with PBS at a ratio of 1:1 and centrifuged on a Ficoll-Paque Plus (GE Healthcare Life Sciences, NJ, USA) to separate the WBC (white blood cell) aggregation layer, and the peripheral blood mononuclear cells were obtained from the separated layer.

In order to evaluate the immune-enhancing effect, the CJLP17 strain was mixed with each type of immune cells obtained using the above method at a ratio of 10:1, and the mixture was incubated at 37° C. in a cell incubator containing 5% $CO_2$ for 20 hours. After completion of the incubation, the cells were centrifuged, and the immune-activating effect of the culture supernatant was evaluated using a cytokine ELISA (Enzyme-linked Immunosorbent Assay). More specifically, the ELISA (R&D Systems, USA) was carried out for IL-12 (interleukin-12), which activates a $T_h1$ (T helper 1)-related immune mechanism that defends against external invasive factors (pathogen). In order to evaluate the $T_h1$ and $T_h2$ immune responses in systemic immunity, splenocytes and peripheral blood monocytes were used for IL-12 and IL-10, and in order to more accurately measure the anti-inflammatory response in the intestine, a TGF-beta ELISA test was performed using cells in Peyer's patches and mesenteric lymphocytes.

The graphs showing the measurement results for IL-12, IL-10 and TGF-beta are shown in FIGS. 4 to 6, respectively. In each graph, the control was used as a negative control without strain treatment.

As a result, as shown in FIGS. 4 to 6, it was confirmed that the CJLP17 strain showed the activity of increasing the secretion of IL-12, IL-10, and TGF-beta by stimulating the immune cells. Therefore, it can be seen that the CJLP17 strain exhibits the effect of simultaneously enhancing the $T_h1$ immune mechanism and the $T_h2$ immune mechanism.

Example 6: Inhibitory Effect Against Viral Infection

In order to measure the inhibitory effect of the CJLP17 strain against viral infection, porcine epidemic diarrhea virus (PEDV, SM98, or KPEDV9 strain) was prepared. Specifically, the virus was proliferated in Vero cells (CCL-81, kidney epithelial cells originated from *Chlorocebus*), and MEM (Eagle's Minimum Essential Medium, Gibco BRL, Grand Island, N.Y., USA), heat-inactivated 10% FBS (fetal bovine serum, v/v) and 1% (v/v) penicillin/streptomycin were used as the media for culturing Vero cells. The Vero cells were incubated as a monolayer, washed twice with the media, and then all of the solutions were removed. The virus was mixed at a level of 0.1 MOI (multiplicity of infection) in FBS-free MEM containing trypsin treated with 5 μg/mL TPCK (N-tosyl-L-phenylalanine chloromethyl ketone), treated with a minimal volume of the prepared culture cells, and then incubated in a 37° C. cell incubator containing 5% $CO_2$ for 2 to 3 days.

The viral infection was determined by the formation of virus syncytia. When a virus syncytium was formed, the virus culture broth was collected within 3 to 6 hours, and the cells were removed using a centrifuge and stored at −80° C. For the calculation of the infection titer of the virus, the Vero cells were incubated in a 96-well plate at a density of $2 \times 10^4$ cells/0.1 mL, and the cells were washed with PBS. Subsequently, the cells were added with a culture broth, in which the virus was subjected to 2-fold serial dilution, and incubated for 24 to 48 hours to confirm viral infection, and the infection titer of the virus was calculated by the Reed & Muench method.

In order to measure the inhibitory effect of the CJLP17 strain against viral infection, the CJLP17 strain and the four types of immune cells, which were extracted in Example 5, were reacted for 20 to 24 hours to obtain a culture broth. Then, the culture broth was independently treated on the 96-well cell culture plate, in which IPEC-J2 was incubated, and incubated in a 37° C. cell incubator containing 5% $CO_2$ for 2 to 4 hours. The PED virus (SM98 or KPEDV9) at a dose of 100 $TCID_{50}$/mL (50% of tissue cell infectious dose) was aliquoted to each plate and incubated for 48 hours. In order to confirm the viral infection, the cell culture plate was fixed with methanol after completion of the culture, stained with crystal violet, and then the wells in which the cells were denatured were examined with a microscope, thereby confirming the viral infection.

TABLE 6

Inhibitory Effect Against PED Virus (SM98/KPEDV9 Strain) of *Lactobacillus plantarum* CJLP17 by Activated Immune Cells

| | mLN | | Peyer's Patches | | PBMC | | Spin | |
| --- | --- | --- | --- | --- | --- | --- | --- | --- |
| | SM98 | KPEDV9 | SM98 | KPEDV9 | SM98 | KPEDV9 | SM98 | KPEDV9 |
| Negative Control | − | − | − | − | − | − | − | − |
| CJLP17 | ++ | ++ | + | ++ | ++ | ++ | + | ++ |

++: Complete inhibition,
+: Partial inhibition,
−: Infected

As a result, as shown in Table 6 and FIG. 7, it was confirmed that when the immune cells of pigs and the Lactobacillus plantarum CJLP17 were treated together, the immune cells were activated by the strain, and the virus infection was remarkably suppressed. Thus, it could be found that when the immune cells were treated in combination with CJLP17, it showed an excellent antiviral activity against PED virus.

Example 7: Confirmation of Effect on Growth and Diarrhea of Livestock

In order to confirm the effect of the *Lactobacillus plantarum* CJLP17 strain on the growth performance and diarrhea incidence rate of livestock when administered via an oral route, an experiment was carried out as follows:

Thirty-two weaned piglets of the age of 21 days were purchased and raised in an incubator farm, in which the temperature of 31±1° C. and 50% humidity are maintained, for 14 days. The feed was given in the form of common crumble feeds without antibiotics, and water was given to be consumed freely. The *Lactobacillus plantarum* CJLP17 strain was produced in the form of freeze-dried powder and stored in a refrigerator, and thoroughly mixed to the crumble feeds for oral administration such that each piglet could ingest the feed in an amount of $10^{10}$ CFU per day. The effects of the strain on piglet productivity and diarrhea/pale stool incidence rate in the weaned piglet test for a total of 14 days are shown in FIGS. 8 and 9.

As a result, it was confirmed that the mean value of ADG of the group of the weaned piglets fed with the feed containing CJLP17 was superior as compared to the control (FIG. 8). In addition, it was confirmed that the group of the weaned piglets fed with the feed containing CJLP17 showed an effect of improving a diarrhea incidence rate of 48%, as compared to the control group (FIG. 9).

Therefore, it can be found that CJLP17 not only increased the growth of the livestock, i.e., productivity, but also exhibited an effect of significantly reducing the diarrhea incidence rate.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A composition comprising (i) a *Lactobacillus plantarum* CJLP17 strain deposited under accession No. KCCM12249P or a culture thereof, and (ii) a cryoprotectant.

2. The composition of claim 1, wherein the strain has an antibacterial activity against pathogenic microorganisms.

3. The composition of claim 2, wherein the pathogenic microorganism is at least one selected from the group consisting of *E. coli*, enterotoxigenic *E. coli*, *Staphylococcus aureus*, *Salmonella typhimurium*, and *Vibrio parahaemolyticus*.

4. The composition of claim 1, wherein the strain increases secretion of cytokines by promoting activation of immune cells.

5. The composition of claim 4, wherein the cytokine is IL-12, IL-10, or TGF-beta.

6. The composition of claim 1, wherein the strain has an antiviral activity against porcine epidemic diarrhea virus (PEDV).

7. The composition of claim 1, wherein the strain promotes growth of livestock or pet, or reduces diarrhea incidence rate when administered to livestock via an oral route.

8. The composition of claim 1, wherein the cryoprotectant is at least one selected from the group consisting of glycerol, trehalose, maltodextrin, skim milk powder, and starch.

9. A feed additive comprising the composition of claim 1.

10. A functional food comprising the composition of claim 1.

11. The composition of claim 1, wherein the strain has acid resistance, bile resistance, and an immune enhancing activity.

12. A method for inhibiting a viral infection, the method comprising administering an effective amount of the composition comprising a *Lactobacillus plantarum* CJLP17 strain deposited under accession No. KCCM12249P or a culture thereof.

13. The method of claim 12, wherein the virus is porcine epidemic diarrhea virus (PEDV).

14. The method of claim 12, wherein the strain has acid resistance, bile resistance, and an immune-enhancing activity.

15. The method of claim 12, wherein the strain has an antibacterial activity against pathogenic microorganisms.

16. The method of claim 15, wherein the pathogenic microorganism is at least one selected from the group consisting of *E. coli*, enterotoxigenic *E. coli*, *Staphylococcus aureus*, *Salmonella typhimurium*, and *Vibrio parahaemolyticus*.

17. The method of claim 12, wherein the strain increases secretion of cytokines by promoting activation of immune cells.

18. The method of claim 12, wherein the cytokine is IL-12, IL-10, or TGF-beta.

19. The method of claim 12, wherein the composition promotes growth of livestock or reduces diarrhea incidence rate when administered to livestock via an oral route.

20. The method of claim 12, wherein the composition further comprises a cryoprotectant or an excipient.

* * * * *

SEQUENCE LISTING

```
<160> NUMBER OF SEQ ID NOS: 3

<210> SEQ ID NO 1
<211> LENGTH: 1333
<212> TYPE: DNA
<213> ORGANISM: Lactobacillus plantarum

<400> SEQUENCE: 1
gacgggcggt gtgtacaagg cccgggaacg tattcaccgc ggcatgctga tccgcgatta      60
ctagcgattc cgacttcatg taggcgagtt gcagcctaca atccgaactg agaatggctt     120
taagagatta gcttactctc gcgagttcgc aactcgttgt accatccatt gtagcacgtg     180
tgtagcccag gtcataaggg gcatgatgat ttgacgtcat ccccaccttc ctccggtttg     240
tcaccggcag tctcaccaga gtgcccaact taatgctggc aactgataat aagggttgcg     300
ctcgttgcgg gacttaaccc aacatctcac gacacgagct gacgacaacc atgcaccacc     360
tgtatccatg tccccgaagg gaacgtctaa tctcttagat ttgcatagta tgtcaagacc     420
tggtaaggtt cttcgcgtag cttcgaatta aaccacatgc tccaccgctt gtgcgggccc     480
ccgtcaattc ctttgagttt cagccttgcg gccgtactcc ccaggcggaa tgcttaatgc     540
gttagctgca gcactgaagg gcggaaaccc tccaacactt agcattcatc gtttacggta     600
tggactacca gggtatctaa tcctgtttgc tacccatact ttcgagcctc agcgtcagtt     660
acagaccaga cagccgcctt cgccactggt gttcttccat atatctacgc atttcaccgc     720
tacacatgga gttccactgt cctcttctgc actcaagttt cccagtttcc gatgcacttc     780
ttcggttgag ccgaaggctt tcacatcaga cttaaaaaac cgcctgcgct cgctttacgc     840
ccaataaatc cggacaacgc ttgccaccta cgtattaccg cggctgctgg cacgtagtta     900
gccgtggctt tctggttaaa taccgtcaat acctgaacag ttactcttaa atatgttctt     960
ctttaacaac agagttttac gagccgaaac ccttcttcac tcacggggcg ttgctccatc    1020
agactttcgt ccattgtgga agattcccta ctgctgcctc ccgtaggagt ttgggccgtg    1080
```

```
tctcagtccc aatgtggccg attaccctct caggttggct acgtatcatt gccatggtga    1140
gccgttacct caccatctag ctaatacgcc gcgggaccat ccaaaagtga tagccgaagc    1200
catctttcaa actcggacca tgcggtccaa gttgttatgc ggtattagca tctgtttcca    1260
ggtgttatcc cccgcttctg ggcaggtttc ccacgtgtta ctcaccagtt cgccactcac    1320
tcaaatgtaa atc                                                        1333

<210> SEQ ID NO 2
<211> LENGTH: 20
<212> TYPE: DNA
<213> ORGANISM: Artificial Sequence
<220> FEATURE:
<223> OTHER INFORMATION: Primer sequence

<400> SEQUENCE: 2
agagtttgat cmtggctcag                                                    20

<210> SEQ ID NO 3
<211> LENGTH: 19
<212> TYPE: DNA
<213> ORGANISM: Artificial Sequence
<220> FEATURE:
<223> OTHER INFORMATION: Primer sequence

<400> SEQUENCE: 3
ggttaccttg ttacgactt                                                     19
```